United States Patent
Comi

Patent Number: 5,740,814
Date of Patent: Apr. 21, 1998

[54] CONDOM IN A NUT NOVELTY

[76] Inventor: Roger Comi, 15920 Meagher St., Fountain Valley, Calif. 92708

[21] Appl. No.: 872,482

[22] Filed: Jun. 7, 1997

[51] Int. Cl.$^6$ .................................................. A61F 6/04
[52] U.S. Cl. ............................ 128/844; 128/918; 206/69
[58] Field of Search ......................... 128/842, 844, 128/918; 604/347–353; 206/69

[56] References Cited

U.S. PATENT DOCUMENTS

| | | | |
|---|---|---|---|
| 1,726,143 | 8/1929 | Eisinger. | |
| 2,321,254 | 6/1943 | Schmid | 206/69 |
| 4,795,033 | 1/1989 | Duffy | 206/457 |
| 4,846,147 | 7/1989 | Benejamin | 604/353 |
| 5,005,336 | 4/1991 | Bloom | 53/401 |
| 5,044,492 | 9/1991 | Auerbach | 206/69 |
| 5,427,233 | 6/1995 | Zinck et al. | 206/69 |
| 5,651,374 | 7/1997 | Wester | 128/844 |
| 5,666,972 | 9/1997 | Gifford | 128/844 |

Primary Examiner—Michael A. Brown
Attorney, Agent, or Firm—Boldstein & Associates

[57] ABSTRACT

A condom in a nut novelty, wherein a condom is contained with a natural nut. The nut is drilled to create a hole. A blade is inserted through the hole to quarter and then macerate the nut meat. The macerated nut meat is removed through the hole. A condom is inserted into the nut shell by introducing a piece of the condom into the hole, and then repeatedly twisting the condom around the hole and pushing the condom into the hole. The hole is sealed, and then painted to match the nutshell. The nut is cracked by the novelty victim to reveal the condom.

6 Claims, 1 Drawing Sheet

5,740,814

CONDOM IN A NUT NOVELTY

BACKGROUND OF THE INVENTION

The invention relates to a condom in a nut novelty. More particularly, the invention relates to a natural nutshell in which a condom is encased and disguised, and a method of making the same.

U.S. Pat. No. 5,005,336 to Bloom discloses the method of making a Hawaiian nutty gram mailing receptacle. This prior art illustrates the patentability of the method of producing a hidden compartment within a coconut.

U.S. Pat. No. 4,795,033 to Duffy discloses a packaging and storage container that resembles a nut but is in fact made of a low density polyethylene material. While this invention serves the purposes of creating a storage space inside a nut-like container, it fails to provide the natural appearance necessary for the novelty herein disclosed.

While these units may be suitable for the particular purpose employed, or for general use, they would not be as suitable for the purposes of the present invention as disclosed hereafter.

SUMMARY OF THE INVENTION

It is an object of the invention to produce a novelty device embodied in a natural nut, which creates a surprise to a person who opens the nut.

It is another object of the invention that the nut is altered to create the surprise, but still has the appearance of an unaltered nut.

It is yet another object of the invention that a condom is encased in the nut, so that when the nut is cracked open, the person cracking the nut is surprised by the unexpected appearance of the condom.

It is a further object of the invention that the novelty is produced from an actual nut which is drilled, cleaned, filled with a condom, sealed, and painted.

The invention is a condom in a nut novelty, wherein a condom is contained with a natural nut. The nut is drilled to create a hole. A blade is inserted through the hole to quarter and then macerate the nut meat. The macerated nut meat is removed through the hole. A condom is inserted into the nut shell by introducing a piece of the condom into the hole, and then repeatedly twisting the condom around the hole and pushing the condom into the hole. The hole is sealed, and then painted to match the nutshell. The nut is cracked by the novelty victim to reveal the condom.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
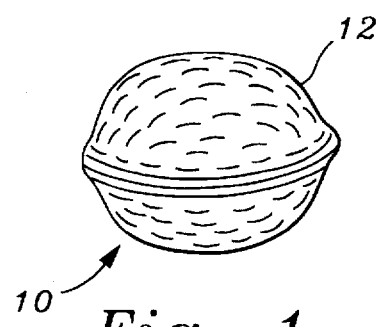
FIG. 1 illustrates an actual nut, ready to be used to produce the condom in a nut novelty device.

FIG. 1 illustrates a nut 10, the nut 10 having a shell 12. The nut 10 as defined herein, is a natural, organic nut, as distinguished from a fake article of manufacture made from plastic or wood. The use of an actual nut assures a consistent, natural appearance, which is necessary to achieve the full effect of the novelty.

An initial step in producing the novelty involves drilling a hole 14 in the shell 12. Preferably the hole 14 is drilled at the end 13, but is illustrated herein elsewhere on the shell 12 for ease of illustration. The hole 14 plays a crucial role in producing the novelty—all steps are performed using the hole 14. The selection of the size of the hole 14 is a trade-off. The larger the hole 14, the easier to perform the steps described hereafter. However, the larger the hole 14, the more conspicuous the tampering is to the novelty "victim". Thus, a ⅜" hole 14 has been selected as an optimum size which allows proper access to the nut interior, but allows the hole 14 to be subsequently disguised.

Figure 2:
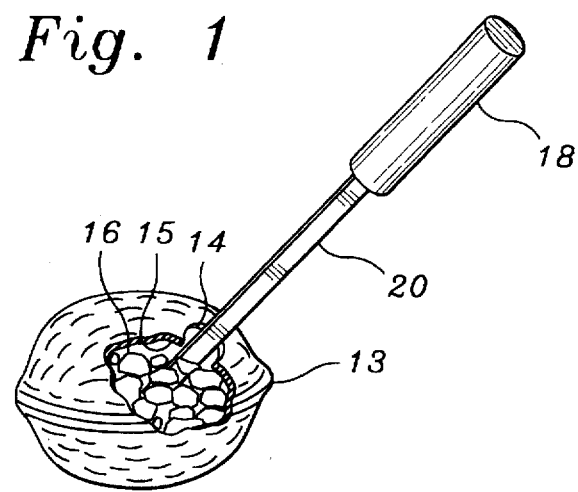
FIG. 2 illustrates a step in producing the novelty, in which a hole has been drilled in the nut, and then a tool is used to macerate the meat within the nut.
Figure 3:
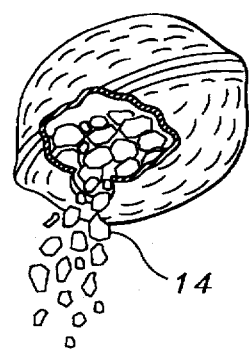
FIG. 3 illustrates a step in producing the novelty, in which the macerated nut meat is removed through the hole.

Referring to FIG. 2, the nut shell 12 defines a nut interior 15. Nut meat 16 is contained within the nut interior 15. An extraction tool 18 is used to macerate the nut meat 16. The extraction tool 18 has a long blade 20 which is approximately ⅜" wide, so that the blade 20 fits within the hole 14, where it can be used to clean the nut interior 15. Cleaning the nut interior 15 involves slicing the meat 16 into quarters with the tool 18, and then further chopping and macerating the nut meat 16 until the resultant pieces are small enough to be removed through the hole 14, as illustrated in FIG. 3.

After the largest pieces of nut meat 16 have been removed, the nut shell 12 is scraped from the inside, to fully clean the nut of stray organics, and ensure a long shelf life for the novelty.

Figure 4:
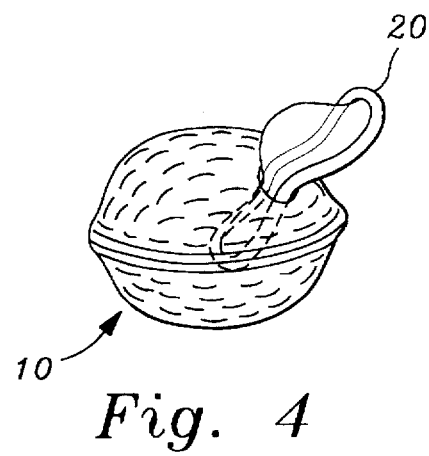
FIG. 4 illustrates a step in producing the novelty, in which a condom is inserted into the nut through the hole.

Following the thorough cleaning of the nut interior 15, a condom 20 is inserted into the nut 10. As illustrated in FIG. 4, getting the condom 20 into the nut 10 involves inserting a portion of the condom 20 into the hole 14, and then repeatedly twisting the condom 20 axially around the hole 14, and pushing the condom 20 into the hole 14 until it is fully within the nut shell 12.

Figure 5:
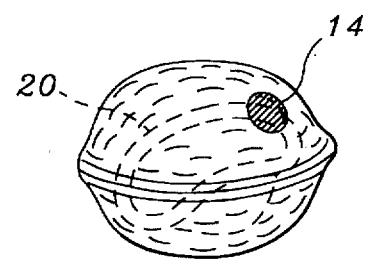
FIG. 5 illustrates the novelty, in which the hole has been filled and sealed.

Once the condom 20 has been fully inserted into the nut shell 12, the hole 14 is sealed and disguised as illustrated in FIG. 5. Sealing the hole 14 is accomplished with a wood putty, which may be precolored to match the nut 10. If ordinary wood putty is used, the hole 14 is disguised by painting over the putty with a paint that is carefully mixed to match the nut shell 12, and its natural coloring.

Figure 6:
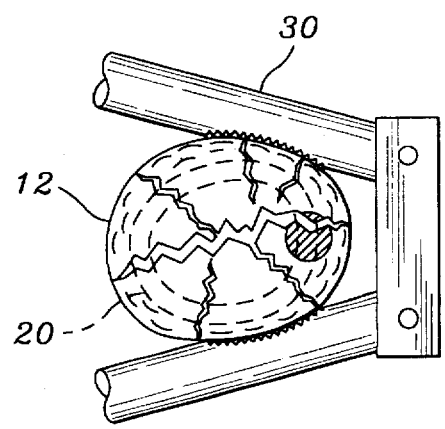
FIG. 6 illustrates the novelty about to be cracked open with a nutcracker, to reveal the condom contained within.

Following the sealing and disguising of the hole 14, the nut shell 12 has a natural appearance, and in fact looks almost identical to an unaltered nut. The nut 10 may be placed among other nuts in a dish or bowl, without drawing suspicion. At some point, an unsuspecting "victim" will crack the nut 10 with a nutcracker 30, as illustrated in FIG. 6. As the nut 10 is cracked, the pieces will fall away, leaving the condom 20. The unexpected appearance of the condom 20 will surprise and amuse the "victim", and others around.

What is claimed is:

1. A novelty, comprising:

a natural nut, the nut having a nutshell; and a condom contained within the nutshell.

2. A nut novelty method, using a natural nut and a condom, comprising the steps of:

drilling a hole in the nutshell;

macerating the nut meat;

removing the nut meat through the hole;

inserting a condom into the nutshell through the hole; and sealing the hole.

3. The nut novelty method as recited in claim 2, using a knife having a blade small enough to fit through the hole, wherein the step of macerating the nut meat further comprises:

inserting the knife through the hole into the nutshell;

quartering the nut meat; and chopping the nut meat into fine particles which are small enough to travel through the hole.

4. The nut novelty as recited in claim 3, wherein the step of sealing the hole further comprises:

filling the hole;

mixing paint to match the nutshell; and painting over the filled hole.

5. The nut novelty as recited in claim 4, wherein the step of inserting the condom into the nutshell through the hole further comprises inserting a piece of the condom into the hole, and then repeatedly:

twisting the condom axially around the hole, and pushing the condom into the hole.

6. The nut novelty as recited in claim 5, further comprising the step of:

cracking the nut to reveal the condom.

* * * * *